United States Patent [19]

Lindblad

[11] Patent Number: 4,801,619
[45] Date of Patent: Jan. 31, 1989

[54] HYALURONIC ACID PREPARATION TO BE USED FOR TREATING INFLAMMATIONS OF SKELETAL JOINTS

[75] Inventor: Gert T. Lindblad, Upsala, Sweden
[73] Assignee: Pharmacia AB, Upsala, Sweden
[21] Appl. No.: 934,410
[22] PCT Filed: Apr. 2, 1986
[86] PCT No.: PCT/SE86/00153
 § 371 Date: Nov. 4, 1986
 § 102(e) Date: Nov. 4, 1986
[87] PCT Pub. No.: WO86/05984
 PCT Pub. Date: Oct. 23, 1986

[30] Foreign Application Priority Data
 Apr. 9, 1985 [SE] Sweden .................. 8501723

[51] Int. Cl.$^4$ .................. C08B 37/05; A61K 31/725
[52] U.S. Cl. .................. 514/825; 514/54; 536/55.1
[58] Field of Search .................. 536/55.1; 514/54, 825

[56] References Cited

U.S. PATENT DOCUMENTS 3,396,081 8/1968 Billek .................. 536/55.1
4,141,973 2/1979 Balazs .................. 536/55.1
4,328,803 5/1982 Pape .................. 514/54
4,517,295 5/1985 Bracke et al. .................. 536/55.1

FOREIGN PATENT DOCUMENTS 0138572 4/1985 European Pat. Off. .
0143393 6/1985 European Pat. Off. .

OTHER PUBLICATIONS

Research in Veterinary Science, vol. 30, No. 2, issued 1981 (Oxford), D. A. Gingerich et al., "Effect of Exogenous Hyaluronic Acid on Joint Function in Experimentally Induced Equine Osteoarthritis: Dosage Titration Studies", see pp. 192-197, especially p. 192 and pp. 196-197 (Discussion).
International Journal of Clinical Pharmacology, Therapy and Toxicology, vol. 20, No. 11, issued 1982 (Munich), O. Namiki et al., "Therapeutic Effect of Intra-Articular Injection of High Molecular Weight Hyaluronic Acid on Osteoarthritis of the Knee", see pp. 501-507, especially p. 501 and pp. 504-506 (Discussion).
Patent Abstracts of Japan, vol. 7, No. 118, C-167, Abstract of JP 58-37001 (A), published 1983-03-04.
Upsala, Journal of Medical Sciences, Supplement 17. issued 1975 (Uppsala), A. Wigren et al., "Repeated Intraarticular Implantation of Hyaluronic Acid", see pp. 1-20, especially p. 3 and p. 19 (Summary).
Proceedings of the Twenty-Fourth Annual Convention of the American Association of Equine Practitioners, St. Louis, Missouri, Dec. 2-6, 1978, published 1979 by American Association of Equine Practitioners, O. G. Swanström, "Hyaluronate (Hyaluronate Acid) and its Use", see pp. 345-348, especially p. 345, first two paragraphs, and p. 347, second paragraph.

Primary Examiner—Ronald W. Griffin
Attorney, Agent, or Firm—Fred Philpitt

[57] ABSTRACT

Hyaluronic acid preparation containing an effective amount of hyaluronic acid of a molecular weight exceeding $3 \times 10^6$ dalton, for intra-articular administration in the treatment of steroid arthropathy and progressive cartilage degeneration caused by proteoglycan degradation.

2 Claims, 1 Drawing Sheet

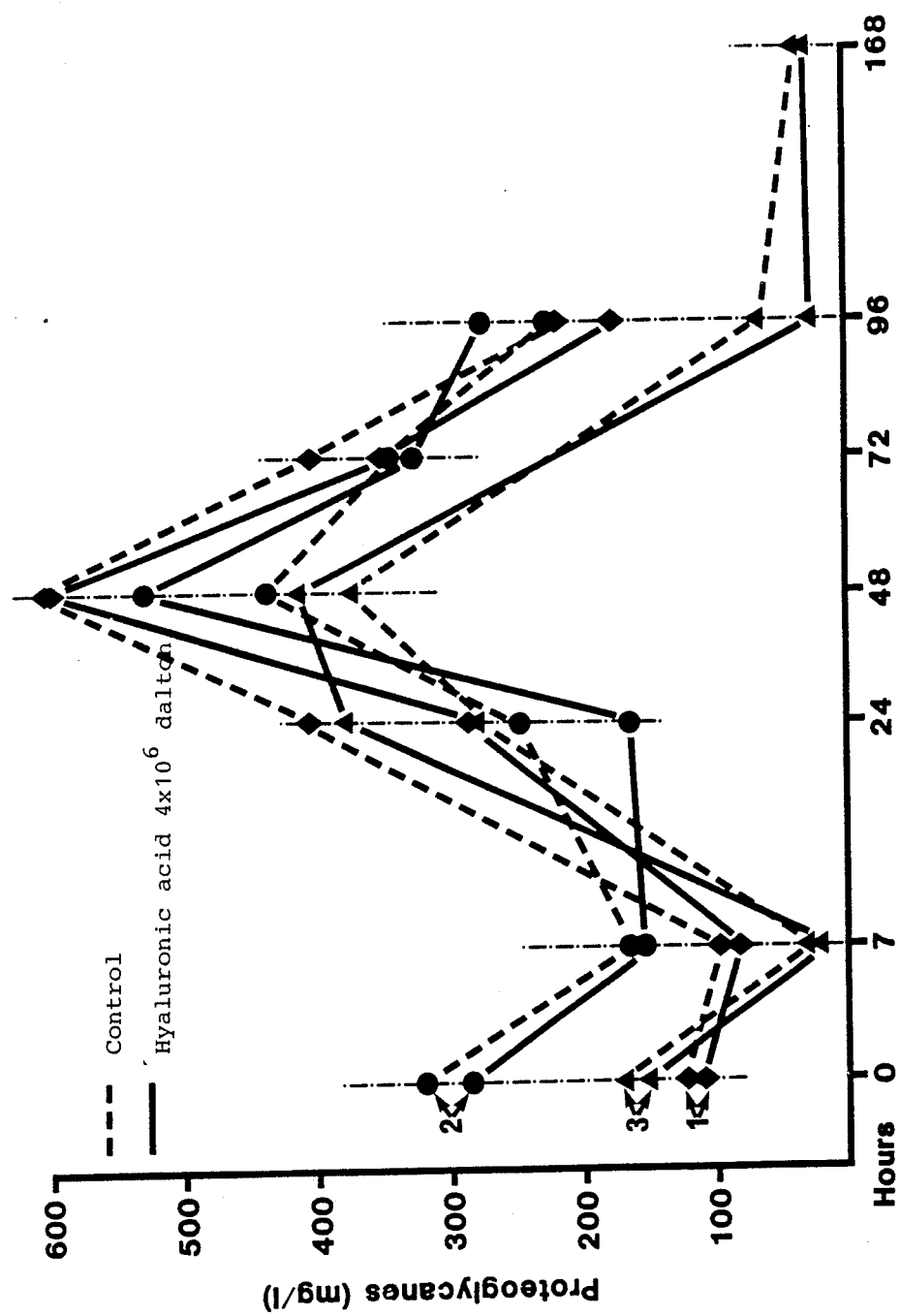

HYALURONIC ACID PREPARATION TO BE USED FOR TREATING INFLAMMATIONS OF SKELETAL JOINTS

This invention relates to high-molecular-weight hyaluronic acid having a molecular weight exceeding $3 \times 10^6$ dalton and intended for use as an agent for counteracting progressive cartilage destruction as, caused by degradation of proteoglycans. The type of treatment here referred to is intended for mammals, including man.

The term "hyaluronic acid", as employed here, refers both to the acid as such and to its physiologically acceptable salt, unless stated otherwise.

The quantitatively predominant part of articular cartilage consists of an extracellular matrix, which plays an important functional role and the composition of which is controlled by a relatively small number of cells. This matrix is composed of (i) collagen forming a fibrous network which is of importance for the volume stability of the tissue, and (ii), proteoglycans as a further major component, having a large amount of mutually repellent electric charges due to which the tissue acquires its elasticity and its ability to resist compression. Moreover, articular cartilage contains several other proteins, generally without known functions. An exception to this are the link proteins which participate in the formation of proteoglycan aggregates and contribute to the stability of these aggregates. Such aggregate formation is a necessary prerequisite for the fixation of the proteoglycans and its negatively charged groups in the tissue.

Degradation of the structures in articular cartilage is a typical characteristic of all diseases resulting in chronic destruction of the joint structures. Examples of such disorders are rheumatoid arthritis, psoriatic arthritis, and osteoarthrosis. Also, acute inflammation of a joint is often accompanied by destruction of the cartilage, although in most cases this will not develop into the chronically destructive disease. It is not known which factors are crucial for the acutely inflamed joint to either proceed to healing or develop into the chronic process. Examples of diseases involving acute joint inflammation are yersinia arthritis, pyrophosphate arthritis, gout arthritis (arthritis urica), septic arthritis and various forms of arthritis of traumatic etiology. Among other factors potentially conducive to the destruction of articular cartilage may be mentioned, for instance, treatment with cortisone; this has been known for a long time to accelerate the degenerative process in osteoarthrosis. Such a so-called "steroid arthropathy" occurs far too often as an undersirable side effect of intra-articular cortisone treatment and can be avoided only by providing for a sufficiently long period of rest after the treatment. Steroid arthropathy is characterized by an advanced degree of articular destruction and X-ray-detectable changes of the same type as occur in advanced degenerative articular disease (Nizolek, DH & White, KK, Cornell Vet. 1981, 71:355–75). According to what is at present accepted as an explanation of the degenerative arthropathy development following treatment with cortisone, this arthropathy is believed to be caused by a primary effect on the chondrocyte metabolism. It should be noted, however, that the actual conditions prevailing in cases of arthritis with severe inflammation of the joint are of a rather more complex character, since in those cases injection of cortisone appears to have an overall positive effect on the clinical picture.

Hyaluronic acid is a naturally occurring glycosaminoglucan. Its molecular weight may vary from 50,000 dalton upwards, and it forms highly viscous solutions. As regards the actual molecular weight of hyaluronic acid in natural biological contexts, this is still a matter of much uncertainty: When the molecular weight of hyaluronic acid is to be determined, different values are obtained depending on the assay method employed, and on the source, the isolation method etc. Molecular weights given in this specification have been determined according to Int J Biol Macromol 7 (1985), p. 30-2. The acid occurs in animal tissue, e.g. spinal fluid, ocular fluid, synovial fluid, cockscombs, skin, and also in some streptococci. Various grades of hyaluronic acid have been obtained. It has been very difficult to obtain a sufficiently pure and high-molecular form suitable for administration in vivo. A preparation with a high degree of purity and entirely free from side effects is the noninflammatory form described in U.S. Pat. No. 4,141,973; this preparation is said to have a molecular weight exceeding 750,000 dalton, preferably exceeding 1,200,000 dalton and has been suggested for therapeutical use in various articular conditions for instance.

Heretofore, Applicant and others have carried out clinical studies on humans in respect of the indication "inflammatory joint conditions". Hyaluronate of a molecular weight substantially lower than $3 \times 10^6$ dalton (for example $10^6$ dalton) was employed in these studies; it was applied by means of intra-articular injections. The accepted therapeutical method for the aforesaid indication is corticosteroid therapy, despite the fact that the effect of these substances is somewhat ambiguous, cf. above. Much work has been done also in the field of veterinary medicine, viz. in horses. Examples of scientific publications describing the use of hyaluronic acid for treatment of articular conditions are Nizolek, DK & White, KK (Cornell Vet. 1981, 71: 355–375); Namiki, O. et al. (Int. J. Chem. Pharmacol., Therapy and Toxicol. 20 /1982/ p. 501-7); Asheim, Å & Lindblad, G (Acta Vet. Scand. 17 /1976/ p. 379–94); Svanström, OG (Proceedings of the 24th annual convention of the American Association of Equine Practitioners; St Louis, Mo., December 1978, Published 1978, p. 345–348); Wigren, A et al (Upsala J Med Sci Suppl 17 (1975) p. 1–20; and Gingerich, DA et al (Res Vet Sci 30 (1980) p. 192–97. In the patent literature hyaluronic acid preparations for general treatment of inflammatory conditions of the joints have been described. Examples are JP-A-No. 58-37001, EP-A-No. 138,572 (Mol. wt. within certain ranges below $10^6$ dalton), and EP-A-No. 143,393 (hyaluronic acid having the following essential characteristics: free of nucleic acid and protein, derived from bacterial sources, and having a controlled Mol. wt. /2–$4 \times 10^6$ dalton mentioned/). It should be noted that both EP-specifications were published during the priority year.

The positive effect of high-molecular-weight hyaluronic acid ($>3 \times 10^6$ dalton) on progressive cartilage destruction involving proteoglycan degradation, has not been mentioned in the Prior Art.

The invention described in EP-A-No. 145,681 has opened up new possibilities for studying early stages of cartilage destruction. The method measures how proteoglycans from cartilage are released into synovial fluid. An increased amount thereof in the synovial fluid is indicative of inceptive destruction, and thus the condition can be diagnosed long before any changes visible on X-ray or through the artroscope, have appeared in the joint. By means of this method it has been possible already at an early stage to monitor the effects exerted by various types of treatment upon the degeneration of cartilage. Our experiments now presented show that hyaluronic acid administered intra-articularly and having a molecular weight of about $3 \times 10^6$ dalton or more is prone to decrease the proteoglycan content of synovial fluid to almost normal levels. This indicates a positive effect on the proteoglycan metabolism of a joint. It has been shown that this is applicable both to inflammatory conditions and to degeneration caused by treatment with symptomatics, such as corticosteroid preparations. It is thus clear that a sufficiently high molecular weight of the hyaluronic acid is apt to counteract side effects that might be caused by corticosteroids or other symptomatics producing similar effects. This finding is quite unexpected, since when corticosteroids are applied, the amount of hyaluronic acid in the synovial cavity will increase substantially (see Experiment 1). Thus the hyaluronic acid employed has an effect far exceeding that of the hyaluronic acid released due to the steroid treatment. Our experiments also show that these hyaluronic acid preparations have a very positive effect on such clinical symptoms as pain, swelling and lameness.

Objects to be attained by this invention are thus to provide improved therapeutical methods for, in the first place, early stages of cartilage degeneration, and to normalize proteoglycan metabolism, e.g. by preventing proteoglycan escape from the cartilage upon treatment with corticosteroids or other symptomatics having a similar effect.

These objectives are attained by intra-articular administration of an effective amount of hyaluronic acid with a mean molecular weight exceeding $3 \times 10^6$ dalton, preferably exceeding $4 \times 10^6$ dalton; but usually the molecular weight will not exceed $7 \times 10^6$ dalton. The dosage of hyaluronic acid administered should preferably be within the range of 5 mg–80 mg. The amount of solution given at each administration is generally less than 60 ml, e.g. less than 20 ml, of an aqueous solution of the acid or its salt. It is convenient to administer the acid dissolved in water (<2% w/w, buffered to physiological pH), for instance in the form of a water-soluble sodium salt. The exact amount will depend on the particular joint to be treated. If the synovial cavity is large, the amounts required lie within the upper part of the aforesaid range, whereas, if the cavity is small, the amounts required are within the lower part of this range. In cases of severe and prolonged disorders, repeated administration may be necessary.

The therapeutic method of the invention may be carried out conjointly with a symptomatics treatment of a type as described above, involving a known administration of a therapeutically active amount of a corticosteroid or other symptomatics having a similar effect. According to the invention, a hyaluronic acid is employed, which has been extracted from animal tissue known to contain hyaluronic acid of a molecular weight exceeding $3 \times 10^6$ dalton. Such hyaluronic acid may also be recovered from cell cultures producing it, e.g. by extraction. Sources that may be used are cockscombs (in the first place from White Leghorn) and certain bacteria, such as streptococci. The ability of a living organism to produce the "right" kind of hyaluronic acid is hereditary; consequently it is always necessary to carefully select individuals within the species employed.

The hyaluronic acid to be employed is heterologous, i.e. derived from a source other than the individual to be treated.

A suitable purification procedure is that described in the aforesaid patent U.S. Pat. No. 4,141,973. Starting out from the right kind of source of raw material, it will be possible to obtain a substantially pure hyluronic acid having a mean molecular weight exceeding $3 \times 10^6$ dalton and having a protein content of less than 0.5% (w/w).

The invention will now be further illustrated by means of a number of non-limitative examples. It will be seen very clearly from the examples that the effect exerted by the hyaluronic acid is very much dependent on the molecular weight of the hyaluronic acid administered. Generally speaking, a very low effect is obtained with molecular weights lower than $1.5 \times 10^6$ dalton, while, generally, a full inhibition of the proteoglycan release due to cartilage degeneration can be obtained in cases where the molecular weight exceeds $3 \times 10^6$ dalton.

EXPERIMENTALS

Clinical situation studied: Steroid arthropathy. The manner in which intra-articularly administered cortisone and hyaluronic acid of various molecular weights will affect the degeneration of cartilage has been studied by means of measuring synovial fluid levels of (i) proteoglycans (according to EP-A-No. 145,681) and (ii) hyaluronic acid (according to Rowley, B. et al., Am. J. Vet. Res. 43 (1982), p. 1096–9).

EXPERIMENT 1

The animals treated were two race horses (trotters) which were no longer being used for racing but were exempt from clinical symptoms of articular problems. The following preparations were employed:

Celestona ®-Bifas ® (liquid for injection, 6 mg of glucocorticoid per ml) (Schering Corp.)

Na-hyaluronate dissolved in water (10 mg/ml, pH7.3, Mol. wt.=$3 \times 10^6$ dalton, produced according to U.S. Pat. No. 4,141,973 from selected White Leghorn roosters /Pharmacia AB, Sweden/)

Physiological saline.

8 joints of each horse were treated; doses given intraarticularly were the following:

| Joint | Treatment |
|---|---|
| Fetlock L.F. (C1) | 4 ml of Celestona ®-Bifas ® |
| U. carpal L.F. (C2) | |
| Fetlock R.F. (P1) | 6 ml of phys. saline |
| U. carpal R.F. (P2) | |
| Fetlock L.L. (H1) | 2 ml of Na—hyaluronate |
| M. carpal L.F. (R2) | |
| Fetlock R.L. (HC1) | 4 ml of Celestona ®-Bifas ® |
| M. carpal R.F. (HC2) | 2 ml of Na—hyaluronate |

3 treatments were carried out: Day 0, after 1 week and after 2 weeks. Synovial fluid was sampled immediately before treatment on day 0, after 1 week and after 2 weeks; and 3 weeks, 4 weeks, 6 weeks and 8 weeks after start. Also, since it was desirable to measure the total amount of proteoglycan fragments and hyaluronic acid in the treated joints, the synovial fluid volumes were measured for this purpose by means of injecting isotope-labeled PVP and measuring the dilution. The results below thus give the total amounts of proteoglycans and Na-hyaluronate per joint.

| Total amount of proteoglycans/joint (μg) | | | | | | | |
|---|---|---|---|---|---|---|---|
| Joint Horse No | L.1/I | L.1/II | P1/I | P1/II | H1/I | H2/II | HC1/I | HC1/II |
| Day 0 | 1 050 | 851 | 1 644 | 674 | 1 110 | 973 | 692 | 732 |
| Week 1 | 22 838 | 15 661 | 1 123 | 865 | 442 | 061 | 14 374 | 2 417 |
| Week 2 | 20 744 | 16 772 | 936 | 680 | 484 | 423 | 13 574 | 1 061 |
| Week 3 | 19 404 | 13 501 | 1 549 | 579 | 399 | 390 | 8 731 | 1 089 |
| Week 4 | 6 193 | 926 | 872 | 477 | 455 | 456 | 1 085 | 428 |
| Week 6 | 1 086 | 441 | 643 | 204 | — | 246 | 253 | 316 |
| Week 8 | 693 | 383 | 623 | 293 | 230 | 260 | 227 | 318 |
| Horse No | C2/I | C2/II | P2/I | P2/II | H2/I | H2/II | HC2/I | HC2/II |
| Day 0 | 1 012 | 890 | 1 033 | 1 022 | 1 067 | 992 | 830 | 606 |
| Week 1 | 15 131 | 9 610 | 735 | 930 | 645 | 843 | 7 120 | 14 663 |
| Week 2 | 27 828 | 22 350 | 580 | 921 | 2 503 | 697 | 7 012 | 9 565 |
| Week 3 | 34 266 | 14 667 | 652 | 752 | 599 | 603 | 7 347 | 9 091 |
| Week 4 | 2 199 | 1 360 | 730 | 677 | 1 104 | 781 | 3 816 | 940 |
| Week 6 | 4 782 | 543 | 344 | 452 | 317 | 383 | 820 | 416 |
| Week 8 | 813 | 591 | 567 | 449 | 531 | 491 | 388 | 380 |

| Total amount of Na—hyaluronate/joint (μg) | | | | | | | |
|---|---|---|---|---|---|---|---|
| Joint Horse No | C1/I | C1/II | P1/I | P1/II | H1/I | H1/II | HC1/I | HC1/II |
| Day 0 | 4 079 | 4 081 | 6 500 | 5 673 | 5 939 | 9 800 | — | 10 481 |
| Week 1 | 14 093 | 8 302 | 4 428 | 3 889 | 3 248 | 7 593 | 19 948 | 10 372 |
| Week 2 | 12 051 | 7 893 | 5 564 | 5 085 | 1 772 | 2 178 | — | 3 081 |
| Week 3 | 7 590 | 10 584 | 7 350 | 4 271 | 2 725 | 2 720 | 23 769 | 3 628 |
| Week 4 | 5 054 | 2 295 | 2 574 | 2 090 | 2 360 | 2 873 | 3 715 | 2 706 |
| Week 6 | 1 213 | 1 534 | 2 530 | 1 125 | — | 2 518 | 1 276 | 3 439 |
| Week 8 | 1 764 | 1 136 | 3 100 | 1 134 | 1 655 | 2 060 | 2 201 | 2 070 |
| Horse No | C2/I | C2/II | P2/I | P2/II | H2/I | H2/II | HC2/I | HC2/II |
| Day 0 | 2 494 | 4 835 | 2 548 | 5 106 | 3 174 | 4 457 | 3 465 | 4 176 |
| Week 1 | 7 900 | 9 091 | 3 007 | 5 472 | 3 978 | 5 414 | 9 900 | 14 935 |
| Week 2 | 14 901 | 11 858 | 3 050 | 4 644 | 5 518 | 2 925 | 14 760 | 13 377 |
| Week 3 | 16 102 | 12 178 | 3 776 | 5 264 | 4 450 | 3 599 | 25 359 | 5 244 |
| Week 4 | 3 323 | 6 588 | 3 338 | 3 575 | 4 477 | 3 348 | 8 848 | 3 820 |
| Week 6 | 4 329 | 4 236 | 2 070 | 3 474 | 1 800 | 2 796 | 3 686 | 3 042 |
| Week 8 | 5 264 | 3 588 | 3 617 | 2 460 | 3 876 | 3 186 | 4 080 | 2 256 |

The experiment shows that cortisone will break up the extracellular matrix in cartilage, thus explaining the known cartilage-degenerative effect of cortisone and/or its negative effect on chondrocytes. Hyaluronic acid having a molecular weight of 3,000,000 will reduce this effect and the duration thereof.

The results show also that cortisone gives rise to an increased amount of hyaluronic acid in the articular cavity.

The below Experiment 2 has been performed for elucidating whether or not the above effect on proteoglycan increase in the articular cavity was coupled to the molecular weight of the Na hyaluronate administered.

EXPERIMENT 2

3 horses (trotters) no longer actively engaged in races have been employed in this test: Horse M, Horse A and Horse H. Each horse was injected intraarticurlarly in the following joints (without any clinical symptoms of disease):

Fetlock joint 1, foreleg (A)
Fetlock joint r, foreleg (B)
Upper carpal 1, foreleg (C)
Upper carpal r, foreleg (D)

The above-enumerated joints of Horse M were treated with 4 ml of Celestona ®-Bifas ® (6 mg of cortisone/ml, Schering Corp.) together with 2 ml of Na hyaluronate having a molecular weight of about $10^5$ dalton (1% in water). The treatment was repeated at intervals of 1 week. Samples for measurement of proteoglycan fragment concentration in the synovial fluid were taken before the start of the treatment and 1 week after the second treatment.

The procedure followed in the case of Horse A was exactly the same except that the Na-hyaluronate had a molecular weight of $6 \times 10^5$ dalton. Also horse H was treated in exactly the same way, but with the exception that the Na-hyaluronate had a molecular weight of $3 \times 10^6$ dalton. Proteoglycan measurements were carried out in a manner analogous to Experiment 1. Results of the analyses (mg/l) are set forth in the Table:

| Time | Joint | Horse M (100 000) | Horse A (600 000) | Horse H (2 700 000) |
|---|---|---|---|---|
| 0 | A | 34,4 | 20,3 | 32,5 |
| | B | 45,9 | 21,1 | 27,9 |
| | C | 33,6  $\bar{x} = 37,2$ | 17,6  $\bar{x} = 21,3$ | 26,6  $\bar{x} = 28,0$ |
| | D | 35,1 | 26,1 | 24,8 |
| after 1 week | A | 534,6 | 374,1 | 311,4 |
| | B | 550,8 | 18,1 | 136,4 |
| | C | 858,6  $\bar{x} = 494,9$ | 101,5  $\bar{x} = 260,5$ | 46,0  $\bar{x} = 130,5$ |
| | D | 35,3 | 548,1 | 28,1 |
| after 2 weeks | A | 350,5 | 169,4 | 54,4 |
| | B | 615,6 | 23,8 | 43,0 |
| | C | 118,9  $\bar{x} = 280,6$ | 20,4  $\bar{x} = 62,7$ | 116,1  $\bar{x} = 58,0$ |
| | D | 37,4 | 37,0 | 18,5 |

The results show that the proteoglycan release (the degeneration) decreases with increasing molecular weights of Na-hyaluronate. When the molecular weights rise above $3 \times 10^6$, the proteoglycan release is hardly measurable at all with the method employed.

EXPERIMENT 3

Two horses, no longer in active training or racing, were used. The actual joints: both fore-fetlock joints in both horses (1 and 2) and both middle carpal divisions in one of them (3), were considered free from clinical signs of arthritis.

After a synovial fluid sample had been withdrawn, 0.5 ml of a 1% Carrageenan solution was injected into each of the abovementioned joints. After 8 hours, the joints were emptied of the synovial fluid and treated: right joints with 2 ml 1% sodium hyaluronate solution (molecular weight $4 \times 10^6$ dalton) and left joints with the same amount of saline. Synovial fluid samples were then withdrawn at the following intervals: 24, 48, 96, 120 and 168 hours.

All joints reacted with a severe synovitis, typified by lameness, swelling, pain and heat. The results of the proteoglycan determinations are shown in FIG. 1.

The hyaluronate-treated joints showed a remarkable clinical improvement immediately after the treatment and could be considered clinically sound within 2 days. The NaCl-treated joints remainded sore with light to moderate signs of swelling, pain and lameness the last follow-up day (7 days after the injection). The results obtained are very interesting and can be interpreted as carrageenan eliciting a proteoglycandegrading effect together with a disturbing effect on the removal of proteoglycans from the synovial fluid.

The invention is characterized in more detail in the attached claims forming an integral part of this specification.

I claim:

1. A method for the treatment of a joint undergoing progressive cartilage degeneration caused by proteoglycan degradation, comprising administering intra-articularly to the said joint a hyaluronic acid preparation containing an effective amount of hyaluronic acid of a molecular weight exceeding $4 \times 10^6$ dalton.

2. A method for preventing steroid arthropathy of a human joint, comprising administering intra-articularly to the said joint a hyaluronic acid preparation containing an effective amount of hyaluronic acid of a molecular weight exceeding $4 \times 10^6$ dalton.

* * * * *